(12) United States Patent
Kappus et al.

(10) Patent No.: US 9,579,117 B2
(45) Date of Patent: Feb. 28, 2017

(54) MULTI-FUNCTION SURGICAL INSTRUMENTS

(71) Applicant: COVIDIEN LP, Mansfield, MA (US)

(72) Inventors: John J. Kappus, Denver, CO (US); David N. Heard, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 469 days.

(21) Appl. No.: 14/276,465

(22) Filed: May 13, 2014

(65) Prior Publication Data

US 2015/0082928 A1 Mar. 26, 2015

Related U.S. Application Data

(60) Provisional application No. 61/882,172, filed on Sep. 25, 2013.

(51) Int. Cl.
*A61B 17/28* (2006.01)
*A61B 17/29* (2006.01)
(Continued)

(52) U.S. Cl.
CPC ............ *A61B 17/29* (2013.01); *A61B 17/295* (2013.01); *A61B 18/1442* (2013.01); *A61B 18/1445* (2013.01); *F16H 21/44* (2013.01); *A61B 2017/2903* (2013.01); *A61B 2017/2903* (2013.01); *A61B 2017/2912* (2013.01); *A61B 2017/2929* (2013.01); *A61B 2018/1455* (2013.01); *A61B 2018/1475* (2013.01); *F16H 21/10* (2013.01); *Y10T 74/18928* (2015.01)

(58) Field of Classification Search
CPC ..... F16H 27/44; F16H 27/10; A61B 18/1445; A61B 18/1442; A61B 2017/2929; A61B 2017/293; A61B 2017/2903; A61B 2017/2912; A61B 2018/1455; A61B 2018/1475; A61B 17/29; A61B 17/295; Y10T 74/18928
USPC .......... 74/103, 107; 606/1, 45–52, 205–207; 600/154
See application file for complete search history.

(56) References Cited

U.S. PATENT DOCUMENTS 5,312,391 A 5/1994 Wilk
5,318,589 A 6/1994 Lichtman
(Continued)

OTHER PUBLICATIONS

European Search Report from corresponding EP 14186363 dated Mar. 3, 2015.

*Primary Examiner* — Christopher D Koharski
*Assistant Examiner* — Michael Carey (57) ABSTRACT

A surgical instrument including housing having a shaft extending distally therefrom, an outer sleeve disposed about the shaft and selectively translatable relative to the shaft, a first drive shaft disposed within the shaft and translatable relative to the shaft independently of the outer sleeve, a second drive shaft disposed within the first drive shaft and coupled to the outer sleeve to translate in conjunction with the outer sleeve, and a rotatable nose wheel. The rotatable nose wheel is mounted about a distal end of the housing and is rotatably coupled to each of the outer sleeve, the shaft, the first drive shaft, and the second drive shaft such that rotation of the rotatable nose wheel effects corresponding rotation of the outer sleeve, the shaft, the first drive shaft, and the second drive shaft in conjunction with one another and relative to the housing.

20 Claims, 9 Drawing Sheets

(51) Int. Cl.
   *F16H 21/44*     (2006.01)
   *A61B 17/295*    (2006.01)
   *A61B 18/14*     (2006.01)
   *F16H 21/10*     (2006.01)

(56) References Cited

U.S. PATENT DOCUMENTS

| | | |
|---|---|---|
| 5,324,254 A | 6/1994 | Phillips |
| 5,401,274 A | 3/1995 | Kusunoki |
| 5,411,519 A | 5/1995 | Tovey et al. |
| 5,445,638 A | 8/1995 | Rydell et al. |
| 5,458,598 A | 10/1995 | Feinberg et al. |
| 5,556,397 A | 9/1996 | Long et al. |
| 5,735,873 A | 4/1998 | MacLean |
| 5,792,164 A | 8/1998 | Lakatos et al. |
| 5,807,393 A | 9/1998 | Williamson, IV et al. |
| 5,893,863 A | 4/1999 | Yoon |
| 5,919,202 A | 7/1999 | Yoon |
| 6,004,319 A | 12/1999 | Goble et al. |
| 6,113,596 A | 9/2000 | Hooven et al. |
| 6,156,009 A | 12/2000 | Grabek |
| 6,190,386 B1 | 2/2001 | Rydell |
| 6,270,497 B1 | 8/2001 | Sekino et al. |
| 6,299,625 B1 | 10/2001 | Bacher |
| 6,387,094 B1 | 5/2002 | Eitenmuller |
| 6,551,313 B1 | 4/2003 | Levin |
| 6,679,882 B1 | 1/2004 | Kornerup |
| 6,808,525 B2 | 10/2004 | Latterell et al. |
| 6,837,888 B2 | 1/2005 | Ciarrocca et al. |
| 6,942,662 B2 | 9/2005 | Goble et al. |
| 7,033,356 B2 | 4/2006 | Latterell et al. |
| 7,063,699 B2 | 6/2006 | Hess et al. |
| 7,128,254 B2 | 10/2006 | Shelton, IV et al. |
| 7,232,440 B2 | 6/2007 | Dumbauld et al. |
| 7,367,976 B2 | 5/2008 | Lawes et al. |
| 7,402,162 B2 | 7/2008 | Ouchi |
| 7,445,621 B2 | 11/2008 | Dumbauld et al. |
| 7,510,562 B2 | 3/2009 | Lindsay |
| 7,588,570 B2 | 9/2009 | Wakikaido et al. |
| 7,658,311 B2 | 2/2010 | Boudreaux |
| 7,758,577 B2 | 7/2010 | Nobis et al. |
| 7,815,636 B2 | 10/2010 | Ortiz |
| 7,819,872 B2 | 10/2010 | Johnson et al. |
| 8,257,352 B2 | 9/2012 | Lawes et al. |
| 8,353,437 B2 | 1/2013 | Boudreaux |
| 2004/0236326 A1 | 11/2004 | Schulze et al. |
| 2005/0187547 A1 | 8/2005 | Sugi |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0182327 A1 | 7/2009 | Unger |
| 2010/0185196 A1 | 7/2010 | Sakao et al. |
| 2010/0185197 A1 | 7/2010 | Sakao et al. |
| 2011/0071525 A1* | 3/2011 | Dumbauld ......... A61B 18/1442 606/51 |
| 2011/0087218 A1 | 4/2011 | Boudreaux et al. |
| 2011/0130757 A1 | 6/2011 | Horlle et al. |
| 2012/0330351 A1 | 12/2012 | Friedman et al. |

* cited by examiner

MULTI-FUNCTION SURGICAL INSTRUMENTS

CROSS REFERENCE TO RELATED APPLICATION

The present application claims the benefit of and priority to U.S. Provisional Application Ser. No. 61/882,172, filed on Sep. 25, 2013, the entire contents of which are incorporated herein by reference.

BACKGROUND

Technical Field

The present disclosure relates to surgical instruments and, more particularly, to multi-function surgical instruments for treating tissue.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween and a rotation wheel for rotating the end effector assembly about a longitudinal axis.

In general, each functional component provided with a surgical instrument requires a corresponding actuating mechanism for actuating that particular component, e.g., a movable handle, trigger, or rotation wheel. As the number of functional components increases, the arrangement, organization, and interplay between the various actuating mechanisms becomes increasingly important.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with aspects of the present disclosure, a surgical instrument is provided. The surgical instrument includes a housing having a shaft extending distally therefrom, an outer sleeve disposed about the shaft and selectively translatable relative to the shaft, a first drive shaft disposed within the shaft and translatable relative to the shaft independently of the outer sleeve, a second drive shaft disposed within the first drive shaft and coupled to the outer sleeve to translate in conjunction with the outer sleeve, and a rotatable nose wheel mounted about a distal end of the housing. The rotatable nose wheel is disposed about the outer sleeve and is rotatably coupled to each of the outer sleeve, the shaft, the first drive shaft, and the second drive shaft such that rotation of the rotatable nose wheel effects corresponding rotation of the outer sleeve, the shaft, the first drive shaft, and the second drive shaft in conjunction with one another and relative to the housing.

In aspects, the rotatable nose wheel includes a transverse bar extending through an interior thereof and each of the outer sleeve, the first drive shaft, and the second drive shaft define longitudinal slots configured to slidably receive the transverse bar to rotatably fix the outer sleeve, the first drive shaft, and the second drive shaft relative to one another and relative to the rotatable nose wheel. In such aspects, the shaft may define an aperture configured to receive the transverse bar to longitudinally and rotatably fix the shaft relative to the rotatable nose wheel.

In aspects, the surgical instrument further includes a first bushing disposed about the outer sleeve. The first bushing includes a pin extending through a longitudinal slot defined within the shaft, the longitudinal slot of the first drive shaft, and engaged within an aperture defined within the second drive shaft to longitudinally fix the outer sleeve and the second drive shaft to one another such that the outer sleeve and the second drive shaft translate in conjunction with one another independently of the shaft and the first drive shaft.

In aspects, an actuator assembly is provided for longitudinally translating the outer sleeve and the second drive shaft between a retracted position and a deployed position. The actuator assembly includes a linkage rotatably fixed relative to the housing and operably engaged to the first bushing for translating the outer sleeve and the second drive shaft relative to the housing regardless of the rotational orientation of the first bushing relative to the linkage.

In aspects, as an alternative to the first bushing, a second bushing is coupled to each of the outer sleeve, the shaft, the first drive shaft, and the second drive shaft in fixed rotational orientation relative thereto. The second bushing includes a pair of flanges rotatably fixed and slidably received within corresponding tracks defined within the rotatable nose wheel such that rotation of the rotatable nose wheel effects corresponding rotation of the outer sleeve, the shaft, the first drive shaft, and the second drive shaft. In such aspects, the second bushing may further include a pin extending therethrough for coupling the second bushing to each of the outer sleeve, the shaft, the first drive shaft, and the second drive shaft.

In aspects, the pin of the second bushing extends through an aperture defined within the outer sleeve, a longitudinal slot defined within the shaft, a longitudinal slot defined within the first drive shaft, and an aperture defined within the second drive shaft to longitudinally fix the second bushing, the outer sleeve, and the second drive shaft to one another such that the second bushing, the outer sleeve, and the second drive shaft translate in conjunction with one another independently of the shaft and the first drive shaft.

In aspects, the surgical instrument further includes an actuator assembly for longitudinally translating the outer sleeve and the second drive shaft between a retracted position and a deployed position. The actuator assembly includes a linkage rotatably fixed relative to the housing and operably engaged to the second bushing for translating the outer sleeve and the second drive shaft regardless of the rotational orientation of the second bushing relative to the linkage.

In aspects, the surgical instrument further includes an end effector assembly mounted at a distal end of the shaft. The rotatable nose wheel is rotatable relative to the housing to rotate the end effector assembly relative to the housing. In such aspects, the first drive shaft may be coupled to the end effector assembly at a distal end of the first drive shaft such that the first drive shaft is translatable relative to the end effector assembly to manipulate the end effector assembly between a first condition and a second condition.

In aspects, a third drive shaft is provided. The third drive shaft is disposed within the second drive shaft and is translatable relative to the shaft independently of the outer sleeve and the first drive shaft. The rotatable nose wheel is rotatably coupled to the third drive shaft such that rotation of the rotatable nose wheel effects corresponding rotation of the outer sleeve, the shaft, the first drive shaft, the second drive shaft, and the third drive shaft in conjunction with one another and relative to the housing.

A surgical instrument provided in accordance with aspects of the present disclosure includes a housing having a shaft extending distally therefrom. The shaft defines a longitudinal slot and an aperture distally of the longitudinal slot. An outer sleeve is slidably disposed about the shaft. The outer sleeve defines a longitudinal slot and an aperture proximally of the longitudinal slot. A first drive shaft is slidably disposed within the shaft. The first drive shaft defines a longitudinal slot. A second drive shaft is disposed within the first drive shaft. The second drive shaft defines a longitudinal slot and an aperture proximally of the longitudinal slot. A bushing is disposed about the outer sleeve. The bushing includes a pin extending through the aperture of the outer sleeve, the longitudinal slot of the shaft, the longitudinal slot of the first drive shaft, and the aperture of the second drive shaft to longitudinally fix the outer sleeve and the second drive shaft to one another and permit translation of the outer sleeve and the second drive shaft relative to the shaft and the first drive shaft. A rotatable nose wheel is mounted about a distal end of the housing. The rotatable nose wheel is disposed about the outer sleeve. The rotatable nose wheel includes a transverse bar extending through the aperture of the shaft and the longitudinal slots of the outer sleeve, the first drive shaft, and the second drive shaft such that rotation of the rotatable nose wheel effects corresponding rotation of the outer sleeve, the shaft, the first drive shaft, and the second drive shaft in conjunction with one another and relative to the housing.

In aspects, an actuator assembly is provided for longitudinally translating the outer sleeve and the second drive shaft between a retracted position and a deployed position. The actuator assembly includes a linkage rotatably fixed relative to the housing and operably engaged to the bushing for translating the outer sleeve and the second drive shaft relative to the housing regardless of the rotational orientation of the bushing relative to the linkage.

In aspects, an end effector assembly is mounted at a distal end of the shaft. The rotatable nose wheel is rotatable relative to the housing to rotate the end effector assembly relative to the housing. The first drive shaft may be coupled to the end effector assembly at a distal end of the first drive shaft. In such aspects, the first drive shaft may be translatable relative to the end effector assembly to manipulate the end effector assembly between a first condition and a second condition.

A surgical instrument provided in accordance with aspects of the present disclosure includes a housing having a shaft extending distally therefrom. The shaft defines a longitudinal slot. An outer sleeve is slidably disposed about the shaft and defines an aperture. A first drive shaft is slidably disposed within the shaft and defines a longitudinal slot. A second drive shaft is disposed within the first drive shaft and defines an aperture. A bushing is disposed about the outer sleeve. The bushing includes a pin extending through the aperture of the outer sleeve, the longitudinal slot of the shaft, the longitudinal slot of the first drive shaft, and the aperture of the second drive shaft to longitudinally fix the outer sleeve and the second drive shaft to one another and permit translation of the outer sleeve and the second drive shaft relative to the shaft and the first drive shaft. The bushing also includes a pair of flanges extending therefrom. A rotatable nose wheel is mounted about a distal end of the housing and is disposed about the outer sleeve. The rotatable nose wheel defines a pair of tracks configured to slidably receive the flanges of the bushing in fixed rotational orientation relative thereto such that rotation of the rotatable nose wheel effects corresponding rotation of the outer sleeve, the shaft, the first drive shaft, and the second drive shaft in conjunction with one another and relative to the housing.

In aspects, the surgical instrument further includes an actuator assembly for longitudinally translating the outer sleeve and the second drive shaft between a retracted position and a deployed position. The actuator assembly includes a linkage rotatably fixed relative to the housing and operably engaged to the bushing for translating the outer sleeve and the second drive shaft regardless of the rotational orientation of the bushing relative to the linkage.

In aspects, the surgical instrument further includes an end effector assembly mounted at a distal end of the shaft. The rotatable nose wheel is rotatable relative to the housing to rotate the end effector assembly relative to the housing. In such aspects, the first drive shaft may be coupled to the end effector assembly at a distal end of the first drive shaft such that the first drive shaft is translatable relative to the end effector assembly to manipulate the end effector assembly between a first condition and a second condition.

In aspects, a third drive shaft is provided. The third drive shaft is disposed within the second drive shaft and is translatable relative to the shaft independently of the outer sleeve and the first drive shaft. The rotatable nose wheel is rotatably coupled to the third drive shaft such that rotation of the rotatable nose wheel effects corresponding rotation of the outer sleeve, the shaft, the first drive shaft, the second drive shaft, and the third drive shaft in conjunction with one another and relative to the housing.

BRIEF DESCRIPTION OF THE DRAWINGS

Various aspects of the present disclosure are described herein with reference to the drawings wherein like reference numerals identify similar or identical elements.

DETAILED DESCRIPTION

Referring now to FIGS. 1-5, a forceps provided in accordance with the present disclosure is shown generally identified by reference numeral 10. Forceps 10 is configured to operate in both a bipolar mode, e.g., for grasping, treating, and/or dissecting tissue, and a monopolar mode, e.g., for treating and/or dissecting tissue, although other configurations are also contemplated. As such, and as will be described in greater detail below, forceps 10 includes multiple actuation assemblies and components configured to facilitate the various operations of forceps 10. In particular, the various actuation assemblies and components of forceps 10 are particularly arranged and configured to minimize the size of the housing of forceps 10, thus allowing a user to readily grasp forceps 10 and manipulate forceps 10 with a single handle, without compromising the functionality of any of the functional components of forceps 10. Further, the actuation shafts and sleeves of the various functional components of forceps 10 are concentrically arranged so as to minimize the diameter of the elongated shaft portion of forceps 10, thus facilitating use of forceps 10 in endoscopic procedures. Alternatively, forceps 10 may be configured for use in open surgical procedures.

Continuing with reference to FIGS. 1-5, forceps 10 includes an outer fixed shaft 12 defining a longitudinal axis "X-X," a housing 20, a handle assembly 30, a trigger assembly 60, a rotating assembly 70, a lever assembly 80, an end effector assembly 100, and a monopolar assembly 200. Outer fixed shaft 12 defines a distal end 14 that is configured to mechanically engage end effector assembly 100 and a proximal end 16 that mechanically engages housing 20. Housing 20 is configured to house the internal working components of forceps 10, which will be descried in detail below. Rotating assembly 70 includes a rotatable nose wheel 72 which is rotatably disposed about the distal end of housing 20. Rotatable nose wheel 72 is rotatable about longitudinal axis "X-X" in either direction to effect corresponding and cooperative rotation of outer fixed shaft 12 (and the internal components therein), end effector assembly 100, and monopolar assembly 200, as will be described in detail below.

Referring to FIGS. 2A-3D, end effector assembly 100 is shown attached at a distal end 14 of outer fixed shaft 12 and includes a pair of opposing jaw members 110 and 120. Each jaw member 110 and 120 includes a distal jaw portion 110a, 120a and a proximal flange portion 110b, 120b extending proximally from the respective distal jaw portion 110a, 120a. Proximal flange portions 110b, 120b of jaw members 110, 120, respectively, are pivotably coupled to one another about a pivot 102. Distal jaw portions 110a, 120a of jaw members 110, 120, respectively, each include an electrically-insulative outer jaw housing 111, 121 and an electrically-conductive plate 112, 122 disposed atop respective jaw housings 111, 121, although other configurations are also contemplated. Plates 112, 122 of jaw members 110, 120, respectively, are adapted to connect to any suitable source of energy (not explicitly shown), e.g., electrosurgical, ultrasonic, microwave, light, etc., for conducting energy therebetween and through tissue grasped between jaw members 110, 120 to treat, e.g., seal, tissue. In one particular configuration, end effector assembly 100 defines a bipolar configuration wherein plate 112 is charged to a first electrical potential and plate 122 is charged to a second, different electrical potential such that an electrical potential gradient is created for conducting energy between plates 112, 122 and through tissue grasped therebetween for treating e.g., sealing, tissue. Activation switch 90 (FIG. 1) is likewise coupled to plates 112, 122, thus allowing the user to selectively apply energy to plates 112, 122 of end effector assembly 100 for treating, e.g., sealing, tissue during a bipolar mode of operation. Forceps 10 may further include a cable 2 (FIG. 1) for connecting end effector assembly 100 to external power and energy sources, or may be configured as a wireless, battery-powered device having power and energy-generating components disposed within housing 20.

Figure 5:
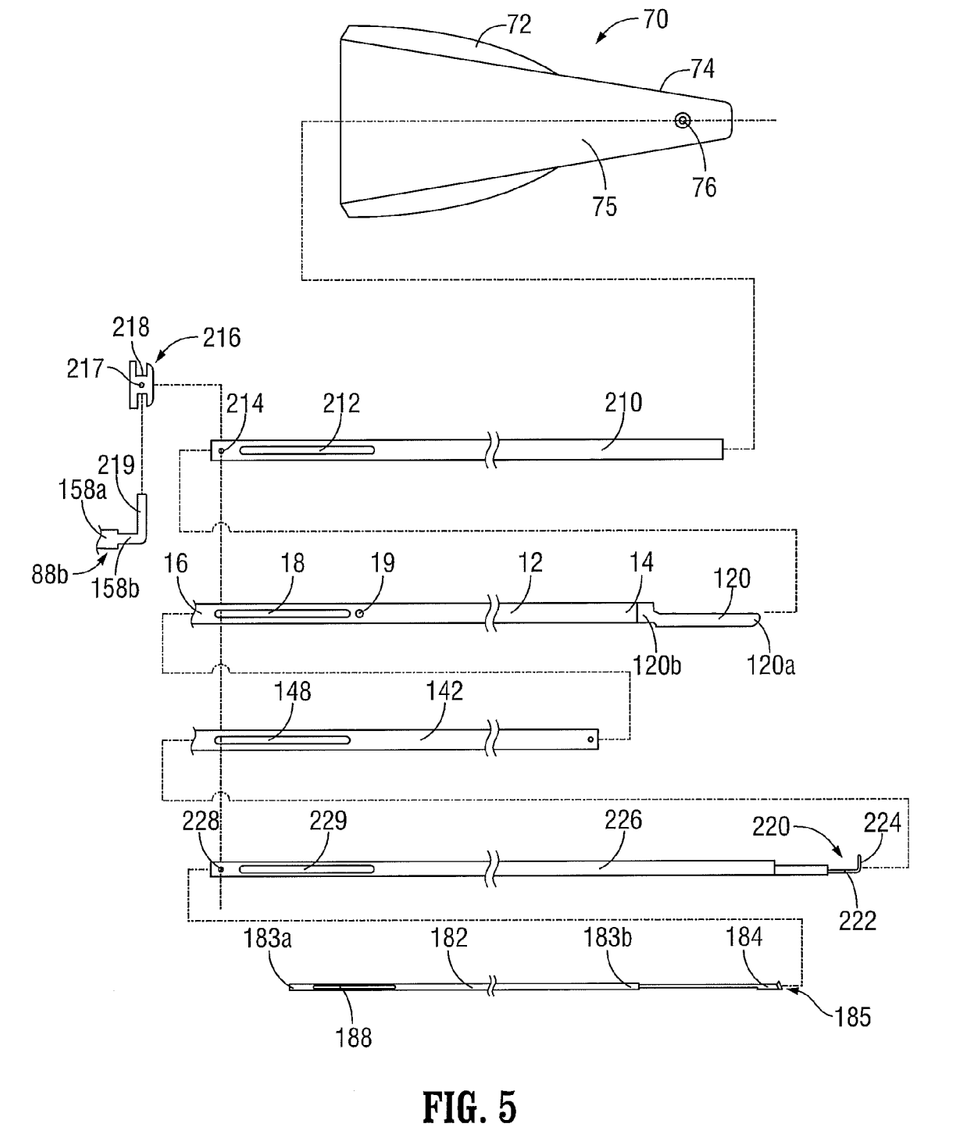
FIG. 5 is an exploded, side view illustrating the arrangement of the actuation assemblies of the forceps of FIG. 1.

End effector assembly 100 is designed as a unilateral assembly, i.e., where jaw member 120 is fixed relative to outer fixed shaft 12 and jaw member 110 is movable relative to outer fixed shaft 12 and fixed jaw member 120. More specifically, jaw member 110 is operably coupled to a drive shaft 142 (FIG. 5) such that proximal translation of drive shaft 142 (FIG. 5) relative to jaw member 110 pulls jaw member 110 to pivot relative to jaw member 120 towards the approximated position, while distal translation of drive shaft 142 (FIG. 5) relative to jaw member 110 urges jaw member 110 to pivot relative to jaw member 120 towards the spaced-apart position (although the reverse configuration or other suitable jaw-drive mechanisms are also contemplated). End effector assembly 100 may alternatively be configured as a bilateral assembly, i.e., where both jaw member 110 and jaw member 120 are movable relative to one another and to outer fixed shaft 12 in response to translation of drive shaft 142 (FIG. 5). In some embodiments, a knife channel 115, 125 may be defined within one or both of jaw members 110, 120 to permit reciprocation of a knife 184 therethrough, e.g., upon actuation of trigger 62 of trigger assembly 60.

With continued reference to FIGS. 2A-3D, one of the jaw members 110, 120 of end effector assembly 100, e.g., jaw member 120, is configured to house energizable rod member 220 of monopolar assembly 200. More specifically, the proximal flange portion of one of the jaw members, e.g., proximal flange portion 120b of jaw member 120, includes an extension portion 126 having a lumen 128a and recess 128b defined therein. Lumen 128a extends through extension portion 126 into communication with recess 128b, which is defined within the distal surface of proximal flange portion 120b of jaw member 120. This configuration of proximal flange portion 120b of jaw member 120 permits body 222 of energizable rod member 220 of monopolar assembly 200 to extend through proximal flange portion 120b of jaw member 120, e.g., through lumen 128a, while also permitting distal tip 224 of rod member 220 of monopolar assembly 200 to be received within recess 128b of proximal flange portion 120b when monopolar assembly 200 is disposed in the retracted position, thereby helping to protect surrounding tissue. The entire proximal flange portion 120b of jaw member 120 or simply extension portion 126 thereof may be formed from an insulative material or may be coated with an insulative material to facilitate the insulation of distal tip 224 of rod member 220 when monopolar assembly 200 is disposed in the retracted position.

Referring again to FIGS. 1-5, monopolar assembly 200 includes an insulative sleeve 210 and an energizable rod member 220. Insulative sleeve 210 is slidably disposed about outer fixed shaft 12 and is configured for translation about and relative to outer fixed shaft 12 between a retracted position (FIGS. 2A and 3A-3C), where insulative sleeve 210 is disposed proximally of end effector assembly 100, and a deployed position (FIGS. 2B and 3D), wherein insulative sleeve 210 is disposed about end effector 100 so as to electrically insulate plates 112, 122 of jaw members 110, 120, respectively, from the surroundings of insulative sleeve 210. Energizable rod member 220 is coupled to an inner shaft 226 disposed within drive shaft 142 of drive assembly 140 for moving energizable rod member 220 between a retracted position, wherein energizable rod member 220 is disposed within recess 128b of extension portion 126 of proximal flange portion 120b of jaw member 120 (FIG. 2A), and a deployed position, wherein energizable rod member 220 extends distally from end effector assembly 100 (FIG. 2B). Energizable rod member 220 is coupled to insulative sleeve 210, as will be described in greater detail below, such that advancement of insulative sleeve 210 between the retracted and deployed positions and advancement of energizable rod member 220 between the retracted and deployed positions are effected concurrently or near concurrently, via actuation of lever assembly 80. Energizable rod member 220 is ultimately coupled to a source of energy for providing energy to distal tip 224 of energizable rod member 220, e.g., upon actuation of activation switch 90 (FIG. 1) in a monopolar mode of operation, for treating tissue using monopolar energy.

With continued reference to FIGS. 1-5, as mentioned above, forceps 10 is a multi-function surgical instrument capable of grasping tissue, dissecting tissue, treating tissue with monopolar energy, and/or treating tissue bipolar energy. In particular, handle assembly 30 is operably coupled to end effector assembly 100 via a drive assembly 140 for selectively pivoting jaw members 110, 120 between the spaced-apart and approximated positions to grasp tissue, trigger assembly 60 is operably coupled to knife assembly 180 for selectively translating knife 184 between jaw members 110, 120 and through tissue grasped therebetween to dissect tissue, and lever assembly 80 is operably coupled to monopolar assembly 200 for selectively moving monopolar assembly 200 between the retracted and deployed positions. Further, rotating assembly 70 is rotatable about longitudinal axis "X-X" to rotate outer fixed shaft 12 (and the internal components therein), end effector assembly 100, and monopolar assembly 200 about longitudinal axis "X-X" and relative to housing 20. Activation switch 90 is operably coupled to plates 112, 122 of jaw members 110, 120, respectively, of end effector assembly 100, and distal tip 224 of energizable rod member 220 of monopolar assembly 200, for selectively supplying energy thereto for treating tissue in a bipolar mode of operation and a monopolar mode of operation, respectively. As will be described below, the arrangement and configuration of these various functional components and assemblies of forceps 10 provides for a minimally-sized housing 20 without compromising functionality.

Handle assembly 30 includes a movable handle 40 and a fixed handle 50. Fixed handle 50 is integrally associated with housing 20. Movable handle 40 includes a lever 42 defining a finger hole 43 and a bifurcated arm 46 extending upwardly from lever 42 and into housing 20. Arm 46 is bifurcated to define first and second spaced-apart flanges that are pivotably coupled to opposed sides of housing 20 via a fixed split pivot 45. Movable handle 40 is pivotable about split pivot 45 and relative to fixed handle 50 between an initial position, wherein movable handle 40 is spaced from fixed handle 50, and a compressed position, wherein movable handle 40 is approximated relative to fixed handle 50. The flanges of arm 46 are each coupled to a distal end of a drive linkage 48 via a first movable pivot 52 that is longitudinally spaced from fixed spit pivot 45. The proximal ends of drive linkages 48, in turn, are pivotably coupled to the free ends of legs 145 of spring cartridge 144 of drive assembly 140 via a second movable pivot 53.

Drive assembly 140 includes a spring cartridge 144 slidably disposed within housing 20, and a drive shaft 142. Drive shaft 142 is coupled to and extends distally from spring cartridge 144, through outer fixed shaft 12 of forceps 10, ultimately coupling to jaw member 110 of end effector assembly 100, as described above. Spring cartridge 144 houses a biasing member (not explicitly shown) that serves to bias drive shaft 142 distally and movable handle 40 towards the initial position, thus biasing jaw members 110, 120 towards the spaced-apart position. Spring cartridge 144 defines a lumen (not explicitly shown) extending longitudinally therethrough that is configured to slidably receive knife drive shaft 182. Spring cartridge 144 further includes a pair of spaced-apart legs 145, which extend proximally from spring cartridge 144. The proximal ends of drive linkages 48, as mentioned above, are pivotably coupled to the free ends of legs 145 of spring cartridge 144. Thus, as movable handle 40 is moved from the initial position towards the compressed position, the flanges of arm 46 urge drive linkages 48 proximally which, in turn, urges legs 145, spring cartridge 144, and drive shaft 142 proximally such that jaw member 110 is pivoted towards the approximated position relative to jaw member 120. Fixed split pivot 45 and first and second movable pivots 52, 53 further cooperate to define an over-center configuration for locking jaw members 110, 120 in the approximated position once movable handle 40 has been sufficiently compressed towards fixed handle 30, e.g., once first movable pivot 52 is disposed above the line segment extending between fixed split pivot 45 and second movable pivot 53.

Trigger assembly 60, as mentioned above, is coupled to knife assembly 180 such that trigger 62 is selectively actuatable from an un-actuated position to an actuated position to advance knife 184 from a storage position (FIG. 3B), wherein knife 184 is disposed proximally relative to jaw members 110, 120, to an extended position, wherein knife 184 extends between jaw members 110, 120 and through knife channels 115, 125, respectively (FIG. 3C), to cut tissue grasped between jaw members 110, 120. Knife assembly 180 includes a knife drive shaft 182 defining proximal and distal ends 183a, 183b, respectively. Proximal end 183a of knife drive shaft 182 is coupled to the proximal base of connectors 68 of trigger assembly 60. Knife drive shaft 182 extends distally between legs 145 of spring cartridge 144, through the lumen (not explicitly shown) of spring cartridge 144, and through inner shaft 226 of monopolar assembly 220, ultimately engaging the proximal end of knife 184. Knife 184 defines a distal cutting edge 185 configured to facilitate the cutting of tissue upon translation of knife 184 between jaw members 110, 120.

Trigger assembly 60 includes a trigger 62 having a toggle member 63 and a bifurcated arm 66 extending upwardly from toggle member 63 and into housing 20. Trigger 62 is pivotably coupled to housing 20 via pivot 65, which extends through an intermediate portion 64 of trigger 62. Arm 66 is bifurcated to define a pair of spaced-apart flanges disposed about spring cartridge 144 of drive assembly 140. A pin 69 pivotably couples each flange of arm 66 of trigger 62 to a connector 68. Connectors 68 extends proximally through housing 20 to the base of connectors 68. The base of connectors 68 is coupled to proximal end 183a of knife drive shaft 182 of knife assembly 180 on either side thereof. The coupling of the base of connectors 68 to knife drive shaft 182 also permits rotation of knife drive shaft 182 relative to connectors 68, the importance of which will become more apparent below. Upon pivoting of trigger 62 about pivot pin 65 and relative to housing 20 from the un-actuated position towards the actuated position, arm 66 is rotated to pull connectors 68 distally such that knife drive shaft 182 is pushed distally to translate knife 184 from the storage position towards the extended position. Return of trigger 62 towards the un-actuated position, on the other hand, pivots arm 66 to push connectors 68 proximally such that knife drive shaft 182 is pulled proximally to translate knife 184 back towards the storage position. A biasing member (not shown) may be provided for biasing trigger 62 towards the un-actuated position, thereby biasing knife 184 towards the retracted position.

Figure 8A:
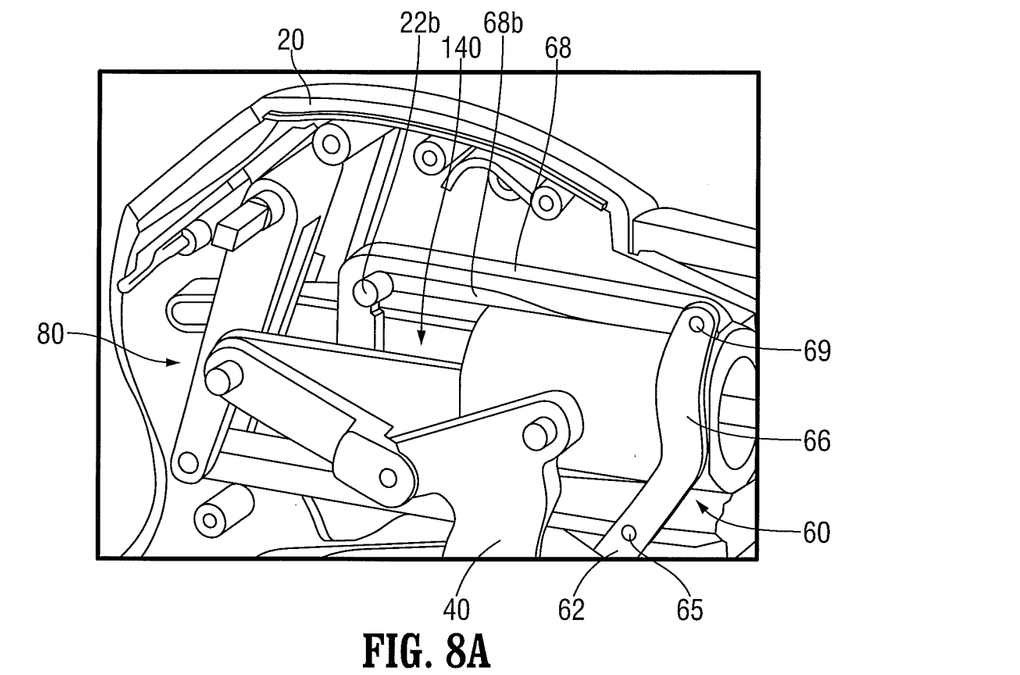
FIG. 8A is an enlarged, top, perspective view of the internal components disposed within the housing of the forceps of FIG. 1.
Figure 8B:
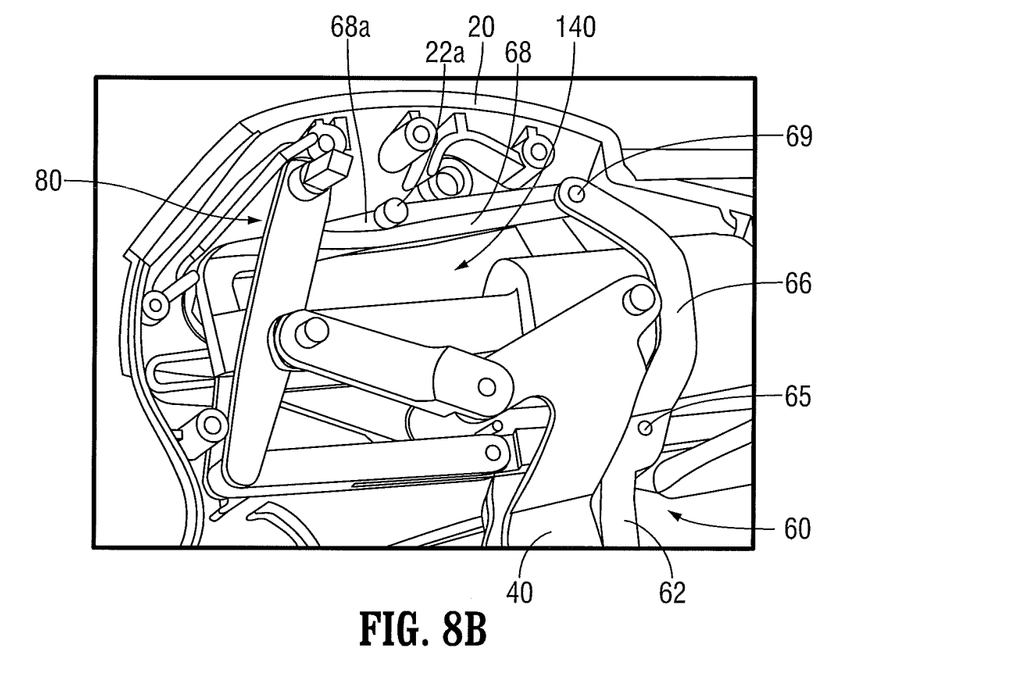
FIG. 8B is an enlarged, bottom, perspective view of the internal components disposed within the housing of the forceps of FIG. 1.

Referring briefly to FIGS. 8A and 8B, connectors 68 of trigger assembly 60 may define a pair of longitudinal grooves 68a, 68b on each side thereof. Housing 20 includes pairs of upper and lower pegs 22a, 22b extending inwardly from opposing sides thereof. Pegs 22a, 22b are configured for slidable receipt within grooves 68a, 68b, respectively, of connectors 68 to guide translation of connectors 68 within housing 20, thereby guiding translation of knife drive shaft 182 and knife 184 (see FIGS. 1-5) between the storage and extended positions.

Referring again to FIGS. 1-5, lever assembly 80 is described. Although lever assembly 80 is shown disposed on only one side of housing 20, lever assembly 80 may be configured to define a symmetrical configuration having substantially similar components disposed on either or both sides of housing 20, thus allowing actuation of lever assembly 80 from either or both sides of housing 20. However, for purposes of simplicity, only one side of lever assembly 80 will be described hereinbelow.

Lever assembly 80 is disposed within a recess 24 defined on an exterior side surface of housing 20 (although lever assembly 80 may also be positioned at any other suitable location) and includes a lever 82 that is rotatable about a pivot 84 between a first position, wherein free end 86 of lever 82 is disposed at a proximal end 25 of recess 24, and a second position, wherein free end 86 of lever 82 is disposed at a distal end 27 of recess 24. As will be described in greater detail below, movement of lever 82 between the first and second positions effects movement of monopolar assembly 200 between the retracted and deployed positions, respectively. Further, a dimple 28 formed within recess 24 of housing 20 may be provided adjacent distal end 27 thereof for receiving a corresponding protrusion (not explicitly shown) extending from an inwardly-facing surface of lever 82 such that, upon movement of lever 82 to the second position, the protrusion (not shown) of lever 82 is engaged within dimple 28 of recess 24 to retain lever 82 in the second position, thereby retaining monopolar assembly 200 in the deployed position. A biasing member (not shown) may be provided for biasing lever 82 towards the first position and, thus, monopolar assembly 200 towards the retracted position, in the absence of lever 82 being locked in the second position via the above-described dimple-protrusion engagement. Other suitable locking mechanisms are also contemplated. In configurations where lever assembly 80 defines a symmetrical configuration, a pair of levers 82 are provided on either side of housing 20, each of which is similar to that described above and is coupled to one end of pivot 84. Pivot 84 extends through housing 20 to operably couple lever 82 to the internal components of lever assembly 80, as will be described below.

Lever assembly 80 includes a pair of spaced-apart lever linkages 87 disposed within housing 20. Lever linkages 87 are coupled at the first ends thereof to pivot 84 such that rotation of lever 82 effects rotation of pivot 84 and, thus, lever linkages 87 in a similar direction. Lever linkages 87 are disposed on either side of knife drive shaft 182 and between legs 145 of spring cartridge 144 of drive assembly 140. Lever linkages 87 are pivotably coupled to a first elongated linkage 88a at the second ends thereof via pivot 89a. First elongated linkage 88a extends distally though housing 20 and is pivotably coupled to a second elongated linkage 88b via a pivot 89b. Second elongated linkage 88b extends further distally through housing 20 and into rotatable nose wheel 72, wherein second elongated linkage 88b couples lever 82 to both outer insulative sleeve 210 and inner shaft 226 of monopolar assembly 200, as will be described in greater detail below. As a result of this configuration, rotation of lever 82 from the first position to the second position rotates lever linkages 87 which, in turn, urge first and second elongated linkages 88a, 88b, respectively, to translate distally though housing 20, thereby moving monopolar assembly 200 from the retracted position to the deployed position.

Forceps 10 further includes a rotatable member 150 operably disposed between second elongated linkage 88b and spring cartridge 144 for moving jaw members 110, 120 to the approximated position (if not already disposed in the approximated position) prior to deployment of monopolar assembly 200 to inhibit unintended interference between end effector assembly 100 and monopolar assembly 200 due to. Rotatable member 150 is rotatably coupled to housing 20 via pivot 152 and includes first and second ends 154, 156, respectively, extending in substantially opposite directions from pivot 152. Rotatable member 150 may be biased, e.g., via a torsion spring (not explicitly shown) or any other suitable biasing member, towards the position shown in FIG. 4A, wherein second end 156 of rotatable member 150 is displaced from spring cartridge 144.

Second elongated linkage 88b defines an expanded body portion 158a compared to distal tip 158b thereof. As a result, with second elongated linkage 88b in the proximal-most position, e.g., with monopolar assembly 200 in the fully retracted position, distal tip 158b of second elongated linkage 88b is positioned adjacent, but spaced-apart from, rotatable member 150. Thus, rotatable member 150 is maintained in the position shown in FIG. 4A, unabated by second elongated linkage 88b. However, when second elongated linkage 88b is translated distally to deploy monopolar assembly 200, body portion 158a of second elongated linkage 88b is urged into contact with first end 154 of rotatable member 150 to rotate rotatable member 150 about pivot 152 and against its bias such that second end 156 of rotatable member 156 contacts and urges spring cartridge 144 distally, thereby effecting pivoting of jaw members 110, 120 to the approximated position (see FIG. 4B). Thus, outer insulative sleeve 210 of monopolar assembly 200 is permitted to slide over end effector assembly 100 without interference from jaw members 110, 120. Upon return of monopolar assembly 200 to the retracted position, second elongated linkage 88b is returned proximally and out of contact with rotatable member 150 such that rotatable member 150 is permitted to return to its biased position, thereby permitting jaw members 110, 120 to return to the spaced-apart position. Other suitable mechanisms for ensuring jaw members 110, 120 are disposed in the approximated position when monopolar assembly 200 is deployed or being deployed are also contemplated.

With continued reference to FIGS. 1-5, as mentioned above, rotating assembly 70 includes a rotatable nose wheel 72 disposed at the distal end of housing 20 and rotatable about longitudinal axis "X-X" to effect corresponding and cooperative rotation of outer fixed shaft 12 (and the internal components therein), end effector assembly 100, and monopolar assembly 200. In order to effect such rotation, rotatable nose wheel 72 is operably coupled to each of the plurality of shafts and sleeves extending through rotatable nose wheel 72, which are variously movable relative to one another and rotatable nose wheel 72.

As best shown in FIG. 5, rotatable nose wheel 72 defines a generally conical body 74 having a hollow interior 75 and a transverse bar 76 extending through hollow interior 75 of body 74. Insulative sleeve 210 of monopolar assembly 200 extends through nose wheel 72 and defines a pair of opposed longitudinal slots 212 towards the proximal end thereof that are configured to receive transverse bar 76 therethrough. This engagement of bar 76 within slots 212 rotatably fixes sleeve 210 relative to nose wheel 72 but permits insulative sleeve 210 to translate longitudinally relative to nose wheel 72, e.g., between a proximal position, wherein transverse bar 76 is disposed at the distal ends of slots 212, and a distal position, wherein transverse bar 76 is disposed at the proximal ends of slots 212. Insulative sleeve 210 further includes a pair of opposed apertures 214 defined therethrough proximally of slots 212. A busing 216 is engaged about insulative sleeve 210 via a pin 217 extending through apertures 214 of insulative sleeve 210. Bushing 216 defines an annular groove 218 configured to receive distal engagement end 219 of second elongated linkage 88b of monopolar assembly 200, thereby coupling second elongated linkage 88b to insulative sleeve 210 regardless of the rotational orientation of insulative sleeve 210 (and, thus, bushing 216) relative to second elongated linkage 88b. Accordingly, with second elongated linkage 88b coupled to bushing 216 of insulative sleeve 210, translation of second elongated linkage 88b can be effected to move insulative sleeve 210 between the retracted and deployed positions.

Fixed shaft 12, which secures fixed jaw member 120 at distal end 14 thereof, is disposed within insulative sleeve 210. More specifically, fixed shaft 12 is rotatably coupled to housing 20 at proximal end 16 thereof and extends through nose wheel 72 and insulative sleeve 210 to fixed jaw 120. Fixed shaft 12 defines a pair of opposed longitudinal slots 18 towards proximal end 16 thereof that are configured to receive pin 217 of bushing 216 therethrough, thus permitting outer sleeve 210 to translate relative to fixed shaft 12. Fixed shaft 12 further defines an aperture 19 configured to receive transverse bar 76 of nose wheel 72 to rotatably fix fixed shaft 12 relative to nose wheel 72 and insulative sleeve 210.

Drive shaft 142 is slidably disposed within fixed shaft 12 and, as mentioned above, is selectively translatable to effect movement of jaw members 110, 120 between the spaced-apart and approximated positions upon actuation of movable handle 40. Drive shaft 142 defines a pair of opposed longitudinal slots 148 that are configured to receive both pin 217 of bushing 216 and transverse bar 76 of nose wheel 72, thus allowing translation of drive shaft 142 and insulative sleeve 210 relative to one another and nose wheel 72, and rotatably securing drive shaft 142 to nose wheel 72. In other words, drive shaft 142 is independently translatable relative to insulative sleeve 210, fixed shaft 12, and nose wheel 72, but is rotatably coupled thereto to rotate in concert therewith.

Inner shaft 226, which supports energizable rod member 220 at the distal end thereof, is slidably disposed within drive shaft 142. Inner shaft 226 includes a pair of opposed apertures 228 defined towards the proximal end thereof and a pair of opposed longitudinal slots 229 disposed towards the proximal end thereof distally of apertures 228. Apertures 228 are configured to receive pin 217 of bushing 216 to fix inner shaft 226 in both rotation and translation relative to outer insulative sleeve 210 and such that movement of second elongated linkage 88b effects corresponding movement of outer insulative sleeve 210 and inner shaft 226. Slots 229 are configured to receive transverse bar 76 to rotatably fix inner shaft 226 relative to nose wheel 72 while still permitting relative translation therebetween.

Knife drive shaft 182 is disposed within inner shaft 226 and is independently translatable relative to inner shaft 226, drive shaft 142, fixed shaft 12, outer insulative sleeve 210, and nose wheel 72, but is rotatably coupled to each via engagement of transverse bar 76 within slots 188 defined within opposed sides of knife drive shaft 182. As can be appreciated in view of the above, rotatable nose wheel 72 is rotatable in either direction about longitudinal axis "X-X" and relative to housing 20 to effect corresponding and cooperative rotation of outer fixed shaft 12 (and the internal components therein), end effector assembly 100, and monopolar assembly 200, without comprising the independent relative movements therebetween.

Figure 6A:
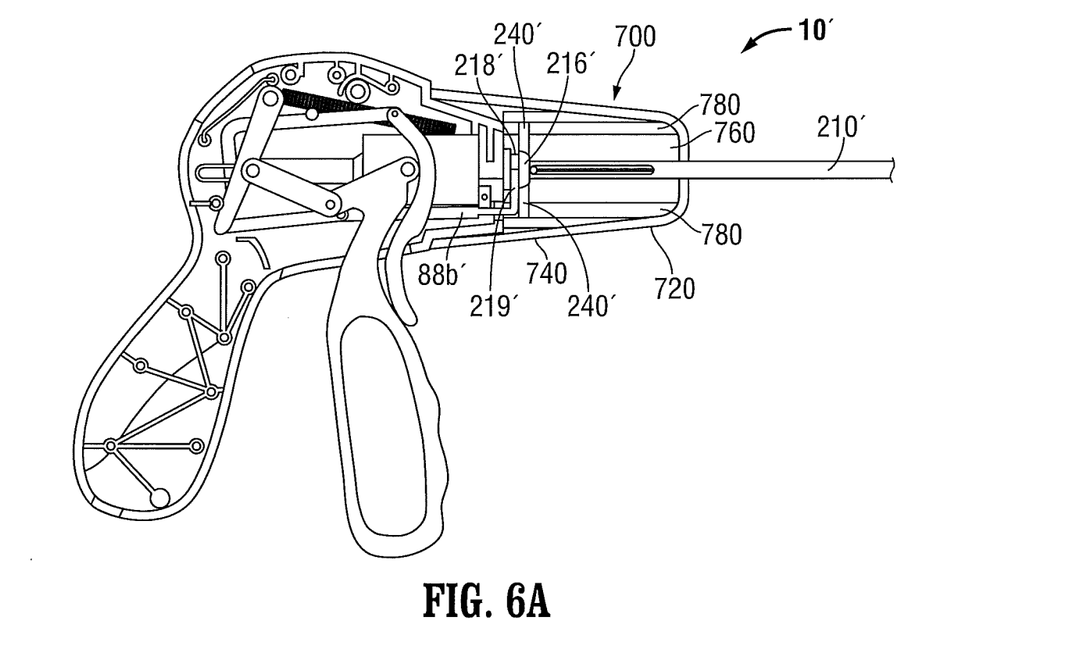
FIG. 6A is a side view of the proximal end of another forceps provided in accordance with the present disclosure shown in a first position, wherein a portion of the housing has been removed to show the internal components thereof.
Figure 6B:
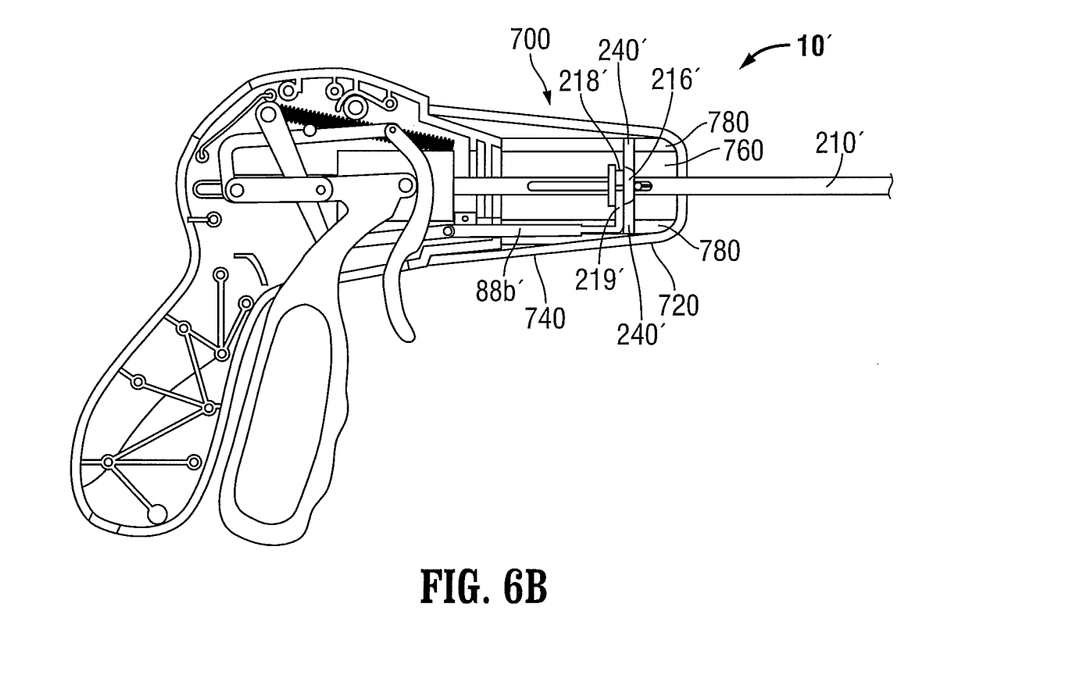
FIG. 6B is a side view of the proximal end of the forceps of FIG. 6A shown in a second position, wherein a portion of the housing has been removed to show the internal components thereof.
Figure 7:
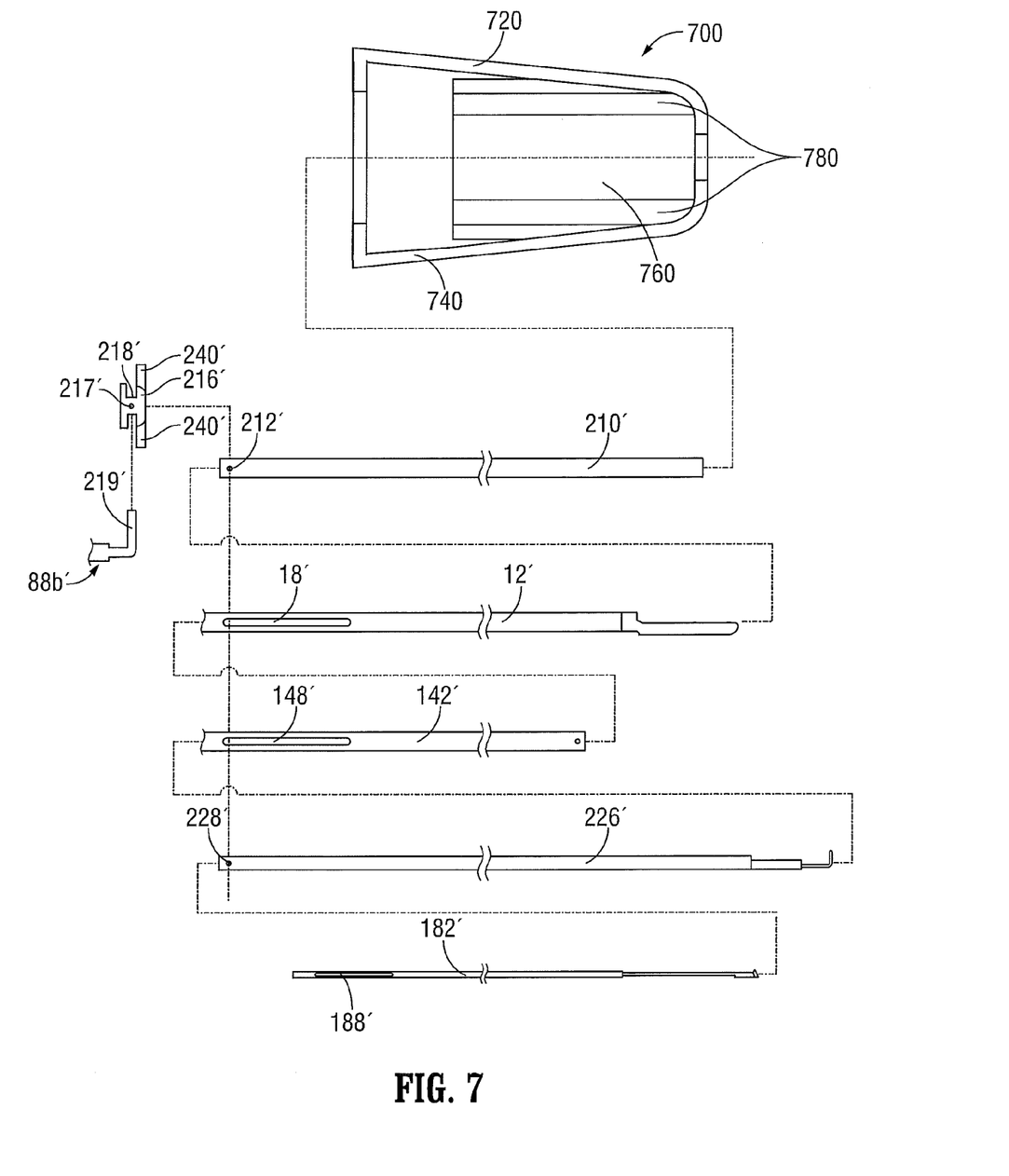
FIG. 7 is an exploded, side view illustrating the arrangement of the actuation assemblies of the forceps of FIGS. 6A-6B.

Turning now to FIGS. 6A-7, another embodiment of a rotating assembly of a multi-function forceps 10' is shown generally identified by reference numeral 700. Forceps 10' is similar to forceps 10 (FIGS. 1-5) except for the features of rotating assembly 700 and the cooperating features that couple rotating assembly 700 to the functional components of forceps 10'. All of the aspects and features of forceps 10 described above are equally applicable to forceps 10', except where specifically contradicted below. For purposes of brevity, similar features which were described above are not repeated hereinbelow.

With continued reference to FIGS. 6A-7, rotating assembly 700 includes a rotatable nose wheel 720 disposed at the distal end of housing 20 and rotatable about longitudinal axis "X-X." Rotatable nose wheel 720 defines a generally cylindrical body 740 having a hollow interior 760 and a pair of opposed longitudinal tracks 780 extending through hollow interior 760 of body 740.

Insulative sleeve 210' extends through nose wheel 720 and includes a pair of opposed apertures 212' defined therethrough towards the proximal end of insulative sleeve 210'. A bushing 216' is engaged about insulative sleeve 210' via a pin 217' extending through apertures 212' of insulative sleeve 210'. Bushing 216' defines an annular groove 218' configured to receive distal engagement end 219' of second elongated linkage 88b'. Bushing 216' further includes a pair of flanges 240' extending in opposite radial directions from bushing 216'. Flanges 240' are configured for receipt within tracks 780 of nose wheel 720 to rotatably fix sleeve 210' relative to nose wheel 720 but permitting sleeve 210' to translate relative to nose wheel 720, e.g., via translation of flanges 240' along tracks 780.

Fixed shaft 12' is rotatably coupled to housing 20' and defines a pair of opposed longitudinal slots 18' configured to receive pin 217' of bushing 216' to rotatably fix fixed shaft 12' relative to nose wheel 720. Drive shaft 142' is slidably disposed within fixed shaft 12' and likewise defines a pair of opposed longitudinal slots 148' configured to receive pin 217' of bushing 216', thus allowing independent translation of drive shaft 142' relative to fixed shaft 12' and insulative sleeve 210', while rotatably coupling drive shaft 142' to nose wheel 720. Inner shaft 226' is slidably disposed within drive shaft 142' and defines a pair of opposed apertures 228' configured to receive pin 217' to fix inner shaft 226' in both rotation and translation relative to outer insulative sleeve 210'. Knife drive shaft 182' is longitudinally movable but rotatably coupled to each of the above shafts and sleeves via engagement of pin 217' within slots 188' defined within opposed sides of knife drive shaft 182'.

As a result of the above-described configuration, rotation of rotatable nose wheel 720 about longitudinal axis "X-X" and relative to housing 20 urges flanges 240' of bushing 216' to rotate similarly, thereby effecting corresponding and cooperative rotation of outer insulative sleeve 210', fixed shaft 12', drive shaft 142', inner shaft 226', and knife drive shaft 182' without interfering with the independent relative movements of these various shafts and sleeves of forceps 10'.

Turning again to FIGS. 1-5, the use and operation of forceps 10 in both the bipolar mode, e.g., for grasping, treating and/or cutting tissue, and the monopolar mode, e.g., for electrical/electromechanical tissue treatment, is described. the use and operation of forceps 10' (FIGS. 6A-7) is similar to that of forceps 10 and, thus, will not be described hereinbelow to avoid unnecessary repetition. Initially, with respect to either mode of operation, forceps 10 is manipulated such that end effector assembly 100 is positioned and oriented as desired within a surgical site. In particular, nose wheel 72 may be rotated to orient end effector assembly 100 and monopolar assembly 200 in a desired orientation. Once positioned as desired, forceps 10 is ready for use.

Figure 3A:
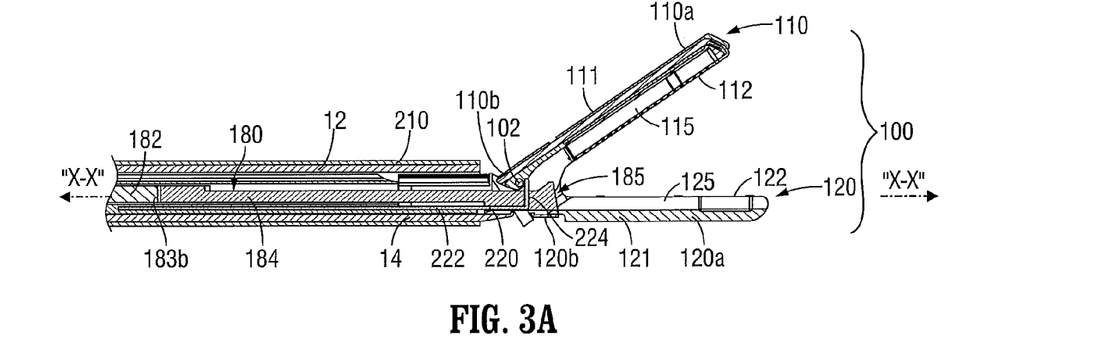
FIG. 3A is a longitudinal, cross-sectional view of the distal end of the forceps of FIG. 1 with the jaw members disposed in the spaced-apart position.
Figure 3B:
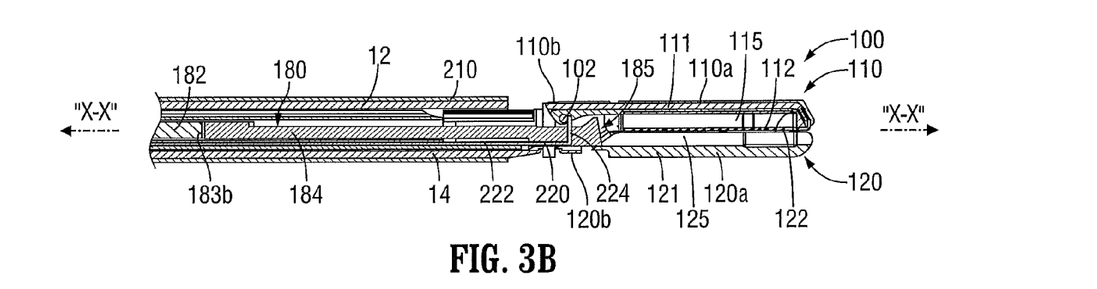
FIG. 3B is a longitudinal, cross-sectional view of the distal end of the forceps of FIG. 1 with the jaw members disposed in an approximated position.

In the bipolar mode, monopolar assembly 200 remains disposed in the retracted position, as shown in FIGS. 2A and 3A-3C. With jaw members 110, 120 disposed in the spaced-apart position, end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween, as shown in FIG. 3B. More specifically, upon actuation of movable handle 40, drive shaft 142 is translated proximally through outer fixed shaft 12, pulling jaw member 110 to pivot relative to jaw member 120 from the spaced-apart position to the approximated position. In this approximated position, energy may be supplied, e.g., via activation of switch 90, to tissue-sealing plate 112 of jaw member 110 and/or tissue-sealing plate 122 of jaw member 120 and conducted through tissue to treat tissue, e.g., to effect a tissue seal or otherwise treat tissue.

Figure 1:
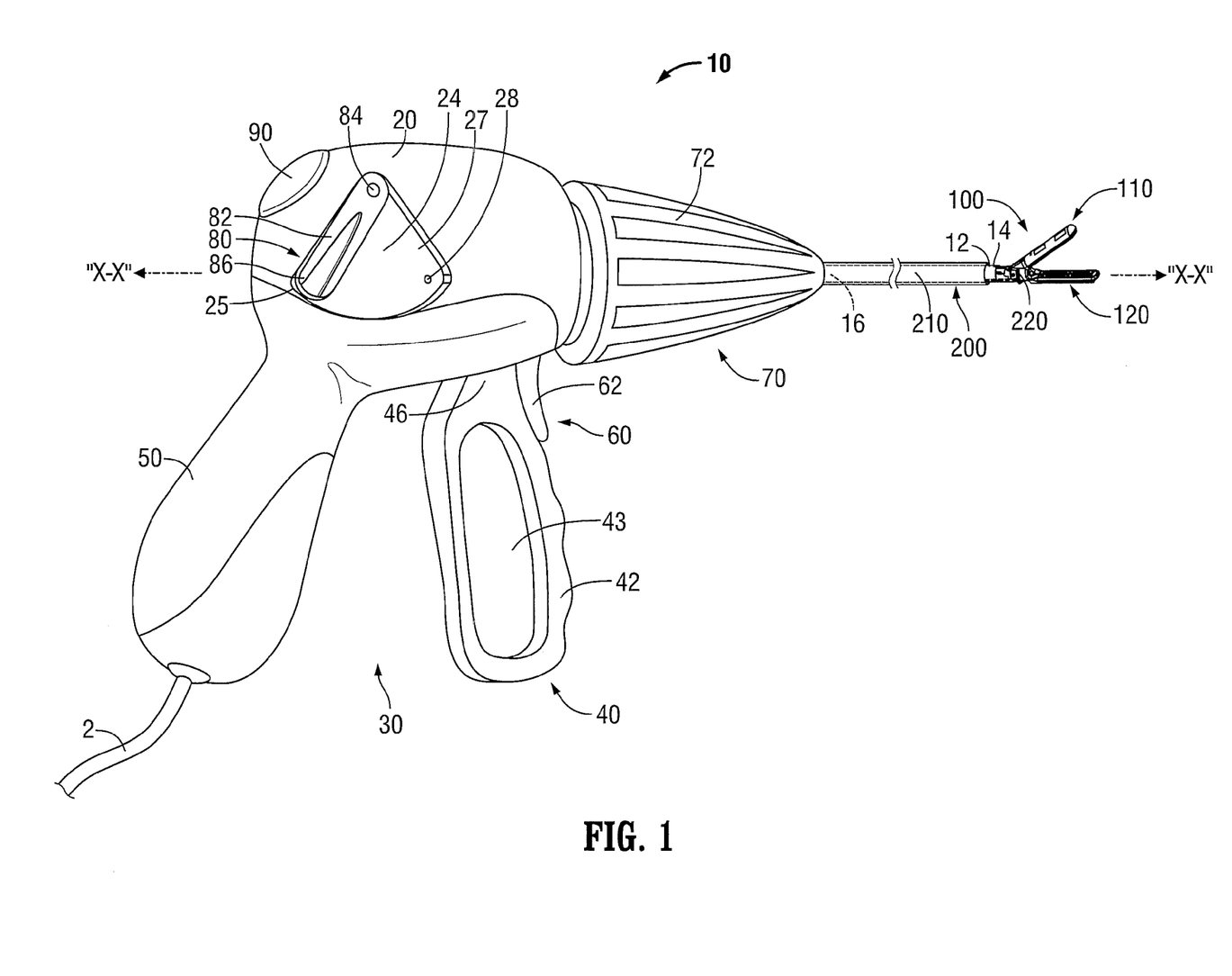
FIG. 1 is a side, perspective view of an endoscopic surgical forceps provided in accordance with the present disclosure.
Figure 2A:
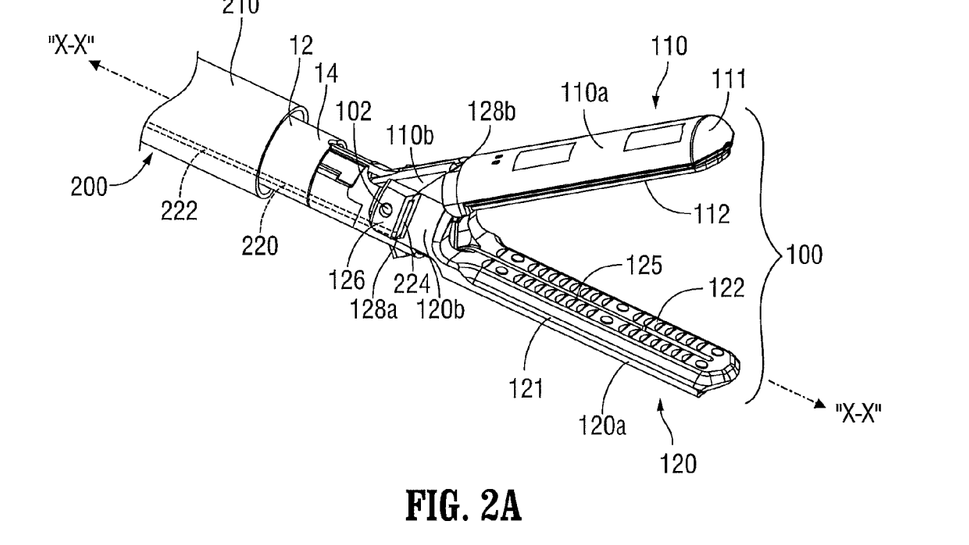
FIG. 2A is an enlarged, perspective view of the end effector assembly of the forceps of FIG. 1 wherein jaw members of the end effector assembly disposed in a spaced-apart position.
Figure 2B:
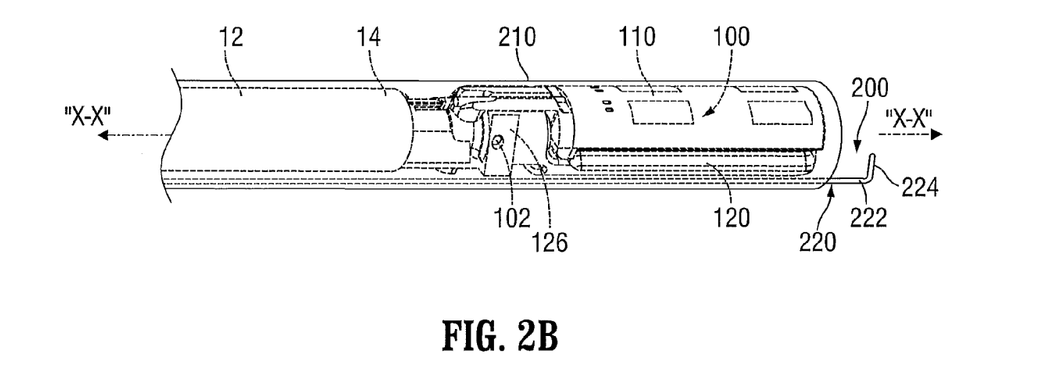
FIG. 2B is an enlarged, perspective view of the end effector assembly of FIG. 2A wherein the jaw members are disposed in an approximated position and wherein the monopolar assembly is disposed in a deployed position.
Figure 3C:
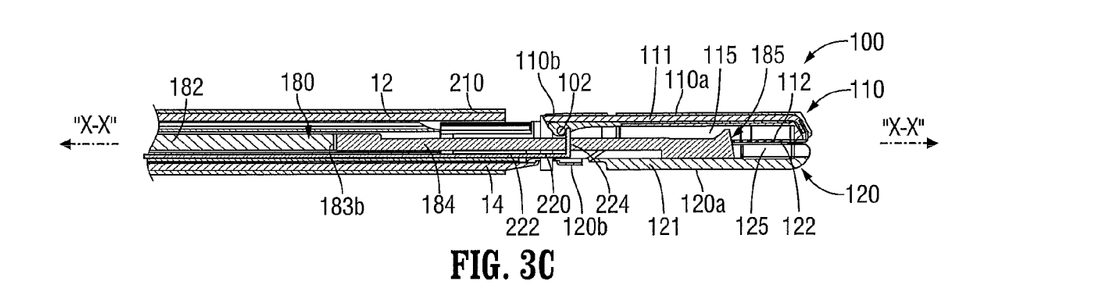
FIG. 3C is a longitudinal, cross-sectional view of the distal end of the forceps of FIG. 1 with the jaw members disposed in the approximated position and the knife disposed in an extended position.

As shown in FIG. 3C, in conjunction with FIG. 1, once tissue treatment is complete (or to cut untreated tissue), knife 184 of knife assembly 180 may be deployed from within outer fixed shaft 12 to between jaw members 110, 120, e.g., via actuation of trigger 82 of trigger assembly 80, to cut tissue grasped therebetween. More specifically, upon actuation of trigger 82, knife drive bar 184 is advanced distally through fixed shaft 12 such that knife 184 extends at least partially through knife channels 115, 125 of jaw members 110, 120, respectively, to cut tissue grasped between jaw members 110, 120. Thereafter, knife 184 may be returned to within outer fixed shaft 12 and jaw members 110, 120 may be moved back to the spaced-apart position (FIG. 3A) to release the treated and/or divided tissue.

With respect to the monopolar mode of operation, movable handle 40 is first depressed relative to fixed handle 50 to pivot jaw member 110 relative to jaw member 120 from the spaced-apart position to the approximated position. However, this step is not a necessity since, as described above, housing 20 includes a rotatable member 150 disposed therein and configured to move jaw members 110, 120 to the approximated position upon deployment of monopolar assembly 200. Once jaw members 110, 120 are disposed in the approximated position, monopolar assembly 200 is translated from the retracted position (FIG. 3B) to the deployed position (FIG. 3D) via movement of lever 82 from the first position to the second position. Upon deployment of monopolar assembly 200, outer insulative sleeve 210 is translated distally over end effector assembly 100 and energizable rod member 220 is translated distally such that distal tip 224 of energizable rod member 220 extends distally from both end effector assembly 100 and outer insulative sleeve 200.

Figure 3D:
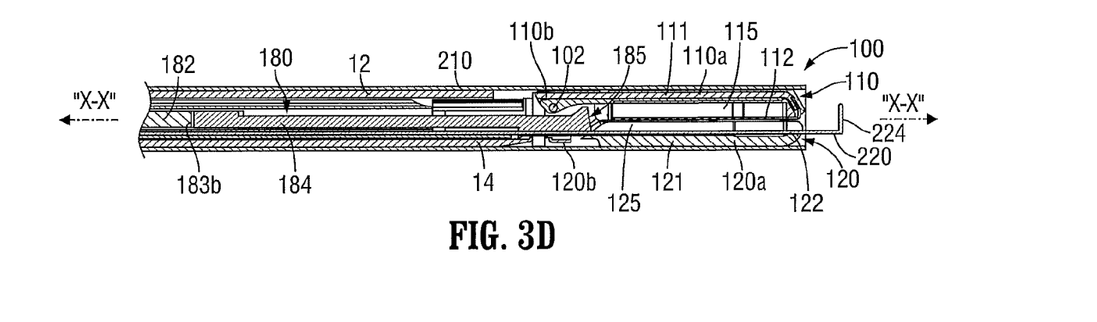
FIG. 3D is a longitudinal, cross-sectional view of the distal end of the forceps of FIG. 1 with the jaw members disposed in the approximated position and the monopolar assembly disposed in the deployed position.
Figure 4A:
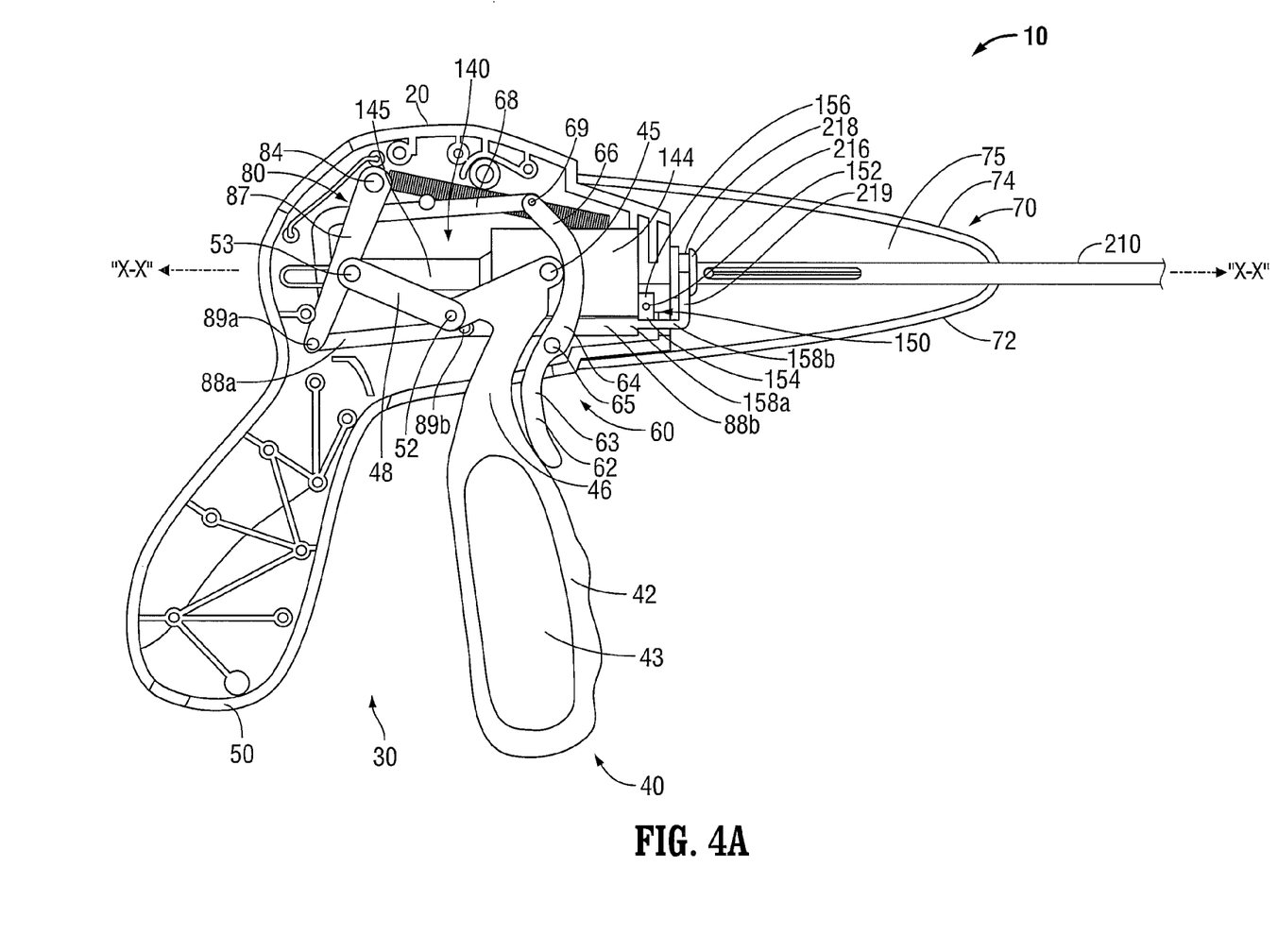
FIG. 4A is a side view of the proximal end of the forceps of FIG. 1 shown in a first position, wherein a portion of the housing has been removed to show the internal components thereof.
Figure 4B:
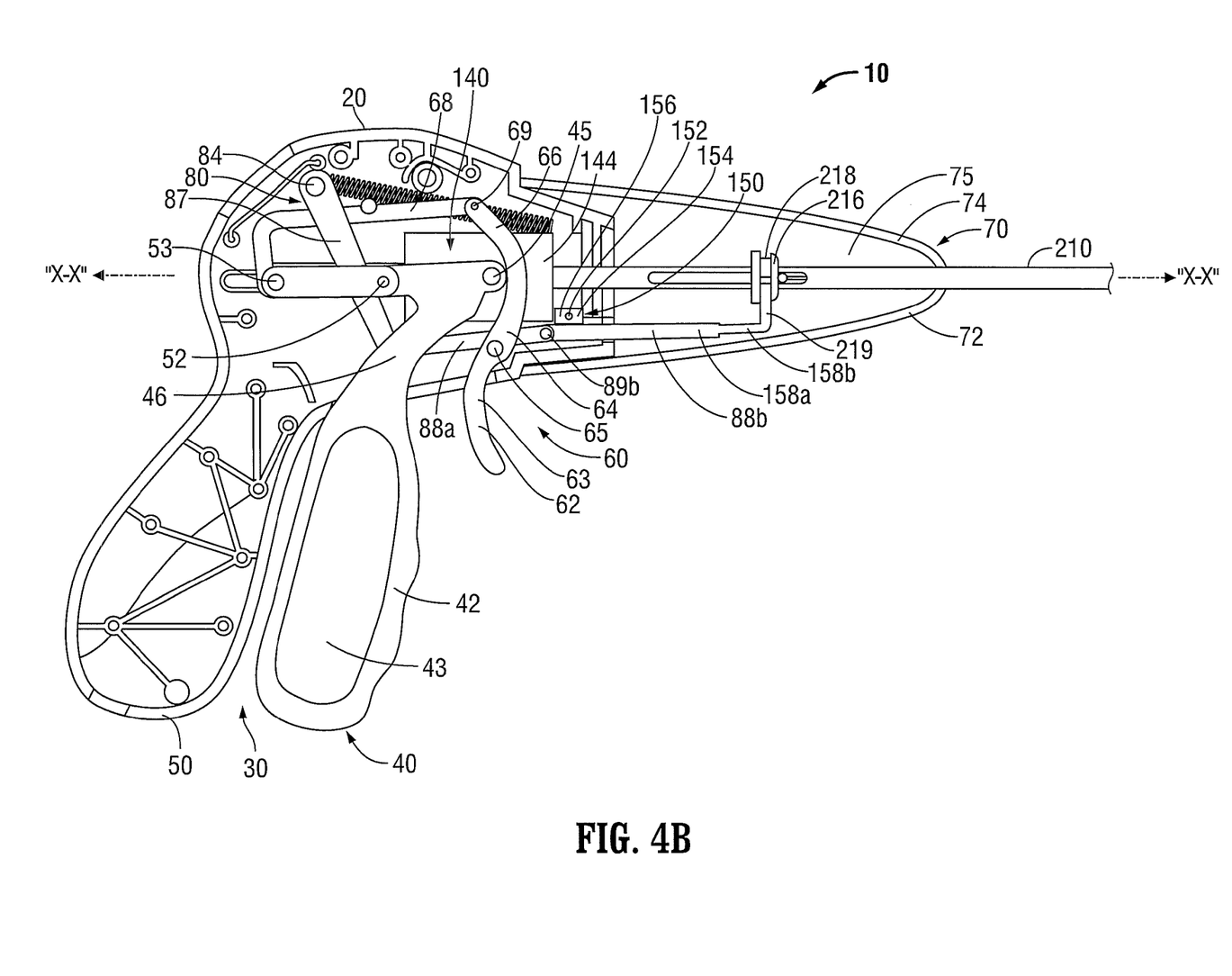
FIG. 4B is a side view of the proximal end of the forceps of FIG. 1 shown in a second position, wherein a portion of the housing has been removed to show the internal components thereof.

With monopolar assembly 200 disposed in the deployed position, as shown in FIG. 3D, activation switch 90 may be actuated to supply energy to distal tip 224 of energizable rod member 220 for treating, e.g., electrically or electromechanically dissecting, tissue. Energy is returned via a remotely positioned return pad (not explicitly shown), although monopolar assembly 200 may alternatively be configured to operate in a biopolar fashion wherein tissue sealing plates 112, 122 are energized to the same potential (but different from the energization of distal tip 224 of energizable rod member 220), thus acting as the return electrode. During application of energy to distal tip 224 of energizable rod member 220, forceps 10 may be moved relative to tissue, e.g., longitudinally along longitudinal axis "X-X" and/or radially therefrom, to facilitate electromechanical treatment of tissue. Alternatively or additionally, forceps 10 may be moved relative to tissue to facilitate mechanically dissecting tissue, e.g., scoring tissue planes, with distal tip 224 in the absence of energy being applied to distal tip 224.

At the completion of tissue treatment, e.g., dissection, monopolar assembly 200 may be returned to the retracted position (FIGS. 3A-3B), e.g., via moving lever 82 back to the initial position. With monopolar assembly 200 once again in the retracted position, jaw members 110, 120 of end effector assembly 100 may one again be manipulated to grasp, treat, and/or cut tissue, as described above, in the bipolar mode.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing having a shaft extending distally therefrom;
an outer sleeve disposed externally about the shaft and selectively translatable relative to the shaft;
a first drive shaft disposed within the shaft and translatable relative to the shaft independently of the outer sleeve;
a second drive shaft disposed within the first drive shaft and coupled to the outer sleeve to translate in conjunction with the outer sleeve; and
a rotatable nose wheel mounted about a distal end of the housing, the rotatable nose wheel disposed about the outer sleeve and rotatably coupled to each of the outer sleeve, the shaft, the first drive shaft, and the second drive shaft such that rotation of the rotatable nose wheel effects corresponding rotation of the outer sleeve, the shaft, the first drive shaft, and the second drive shaft in conjunction with one another and relative to the housing.

2. The surgical instrument according to claim 1, wherein the rotatable nose wheel includes a transverse bar extending through an interior thereof and wherein each of the outer sleeve, the first drive shaft, and the second drive shaft define longitudinal slots configured to slidably receive the transverse bar to rotatably fix the outer sleeve, the first drive shaft, and the second drive shaft relative to one another and relative to the rotatable nose wheel.

3. The surgical instrument according to claim 2, wherein the shaft defines an aperture configured to receive the transverse bar to longitudinally and rotatably fix the shaft relative to the rotatable nose wheel.

4. The surgical instrument according to claim 2, further comprising a first bushing disposed about the outer sleeve, the first bushing including a pin extending through a longitudinal slot defined within the shaft, the longitudinal slot of the first drive shaft, and engaged within an aperture defined within the second drive shaft to longitudinally fix the outer sleeve and the second drive shaft to one another such that the outer sleeve and the second drive shaft translate in conjunction with one another independently of the shaft and the first drive shaft.

5. The surgical instrument according to claim 4, further comprising an actuator assembly for longitudinally translating the outer sleeve and the second drive shaft between a retracted position and a deployed position, the actuator assembly including a linkage rotatably fixed relative to the housing and operably engaged to the first bushing for translating the outer sleeve and the second drive shaft relative to the housing regardless of the rotational orientation of the first bushing relative to the linkage.

6. The surgical instrument according to claim 1, further comprising a second bushing coupled to each of the outer sleeve, the shaft, the first drive shaft, and the second drive shaft in fixed rotational orientation relative thereto, the second bushing including a pair of flanges rotatably fixed and slidably received within corresponding tracks defined within the rotatable nose wheel such that rotation of the rotatable nose wheel effects corresponding rotation of the outer sleeve, the shaft, the first drive shaft, and the second drive shaft.

7. The surgical instrument according to claim 6, wherein the second bushing includes a pin extending therethrough for coupling the second bushing to each of the outer sleeve, the shaft, the first drive shaft, and the second drive shaft.

8. The surgical instrument according to claim 7, wherein the pin of the second bushing extends through an aperture defined within the outer sleeve, a longitudinal slot defined within the shaft, a longitudinal slot defined within the first drive shaft, and an aperture defined within the second drive shaft to longitudinally fix the second bushing, the outer sleeve, and the second drive shaft to one another such that the second bushing, the outer sleeve, and the second drive shaft translate in conjunction with one another independently of the shaft and the first drive shaft.

9. The surgical instrument according to claim 8, further comprising an actuator assembly for longitudinally translating the outer sleeve and the second drive shaft between a retracted position and a deployed position, the actuator assembly including a linkage rotatably fixed relative to the housing and operably engaged to the second bushing for translating the outer sleeve and the second drive shaft regardless of the rotational orientation of the second bushing relative to the linkage.

10. The surgical instrument according to claim 1, further comprising an end effector assembly mounted at a distal end of the shaft, the rotatable nose wheel rotatable relative to the housing to rotate the end effector assembly relative to the housing.

11. The surgical instrument according to claim 1, wherein the first drive shaft is coupled to the end effector assembly at a distal end of the first drive shaft, the first drive shaft translatable relative to the end effector assembly to manipulate the end effector assembly between a first condition and a second condition.

12. The surgical instrument according to claim 1, further comprising a third drive shaft disposed within the second drive shaft, the third drive shaft translatable relative to the shaft independently of the outer sleeve and the first drive shaft, wherein the rotatable nose wheel is rotatably coupled to the third drive shaft such that rotation of the rotatable nose wheel effects corresponding rotation of the outer sleeve, the shaft, the first drive shaft, the second drive shaft, and the third drive shaft in conjunction with one another and relative to the housing.

13. A surgical instrument, comprising:
a housing having a shaft extending distally therefrom, the shaft defining a longitudinal slot and an aperture distally of the longitudinal slot;
an outer sleeve slidably disposed externally about the shaft, the outer sleeve defining a longitudinal slot and an aperture proximally of the longitudinal slot;
a first drive shaft slidably disposed within the shaft, the first drive shaft defining a longitudinal slot;
a second drive shaft disposed within the first drive shaft, the second drive shaft defining a longitudinal slot and an aperture proximally of the longitudinal slot;
a bushing disposed about the outer sleeve, the bushing including a pin extending through the aperture of the outer sleeve, the longitudinal slot of the shaft, the longitudinal slot of the first drive shaft, and the aperture of the second drive shaft to longitudinally fix the outer sleeve and the second drive shaft to one another and permit translation of the outer sleeve and the second drive shaft relative to the shaft and the first drive shaft; and a rotatable nose wheel mounted about a distal end of the housing and disposed about the outer sleeve, the rotatable nose wheel including a transverse bar extending through the aperture of the shaft and the longitudinal slots of the outer sleeve, the first drive shaft, and the second drive shaft such that rotation of the rotatable nose wheel effects corresponding rotation of the outer sleeve, the shaft, the first drive shaft, and the second drive shaft in conjunction with one another and relative to the housing.

14. The surgical instrument according to claim 13, further comprising an actuator assembly for longitudinally translating the outer sleeve and the second drive shaft between a retracted position and a deployed position, the actuator assembly including a linkage rotatably fixed relative to the housing and operably engaged to the bushing for translating the outer sleeve and the second drive shaft relative to the housing regardless of the rotational orientation of the bushing relative to the linkage.

15. The surgical instrument according to claim 13, further comprising an end effector assembly mounted at a distal end of the shaft, the rotatable nose wheel rotatable relative to the housing to rotate the end effector assembly relative to the housing.

16. The surgical instrument according to claim 13, wherein the first drive shaft is coupled to the end effector assembly at a distal end of the first drive shaft, the first drive shaft translatable relative to the end effector assembly to manipulate the end effector assembly between a first condition and a second condition.

17. A surgical instrument, comprising:
a housing having a shaft extending distally therefrom, the shaft defining a longitudinal slot;
an outer sleeve slidably disposed externally about the shaft, the outer sleeve defining an aperture;
a first drive shaft slidably disposed within the shaft, the first drive shaft defining a longitudinal slot;
a second drive shaft disposed within the first drive shaft, the second drive shaft defining an aperture;

a bushing disposed about the outer sleeve, the bushing including a pin extending through the aperture of the outer sleeve, the longitudinal slot of the shaft, the longitudinal slot of the first drive shaft, and the aperture of the second drive shaft to longitudinally fix the outer sleeve and the second drive shaft to one another and permit translation of the outer sleeve and the second drive shaft relative to the shaft and the first drive shaft, the bushing including a pair of flanges extending therefrom; and a rotatable nose wheel mounted about a distal end of the housing and disposed about the outer sleeve, the rotatable nose wheel defining a pair of tracks configured to slidably receive the flanges of the bushing in fixed rotational orientation relative thereto such that rotation of the rotatable nose wheel effects corresponding rotation of the outer sleeve, the shaft, the first drive shaft, and the second drive shaft in conjunction with one another and relative to the housing.

18. The surgical instrument according to claim 17, further comprising an actuator assembly for longitudinally translating the outer sleeve and the second drive shaft between a retracted position and a deployed position, the actuator assembly including a linkage rotatably fixed relative to the housing and operably engaged to the bushing for translating the outer sleeve and the second drive shaft relative to the housing regardless of the rotational orientation of the bushing relative to the linkage.

19. The surgical instrument according to claim 17, further comprising an end effector assembly mounted at a distal end of the shaft, the rotatable nose wheel rotatable relative to the housing to rotate the end effector assembly relative to the housing.

20. The surgical instrument according to claim 17, wherein the first drive shaft is coupled to the end effector assembly at a distal end of the first drive shaft, the first drive shaft translatable relative to the end effector assembly to manipulate the end effector assembly between a first condition and a second condition.

* * * * *